US008720209B1

(12) United States Patent
Beer et al.

(10) Patent No.: US 8,720,209 B1
(45) Date of Patent: May 13, 2014

(54) SOLID STATE RAPID THERMOCYCLING

(75) Inventors: Neil Reginald Beer, Pleasanton, CA (US); Christopher Spadaccini, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 237 days.

(21) Appl. No.: 13/267,777

(22) Filed: Oct. 6, 2011

Related U.S. Application Data

(60) Provisional application No. 61/390,383, filed on Oct. 6, 2010, provisional application No. 61/390,415, filed on Oct. 6, 2010, provisional application No. 61/390,425, filed on Oct. 6, 2010, provisional application No. 61/390,433, filed on Oct. 6, 2010, provisional application No. 61/390,441, filed on Oct. 6, 2010, provisional application No. 61/390,452, filed on Oct. 6, 2010, provisional application No. 61/512,393, filed on Jul. 27, 2011.

(51) Int. Cl.
*B01L 3/00* (2006.01)

(52) U.S. Cl.
USPC ............ 62/3.3; 62/3.2; 62/3.7; 422/943

(58) Field of Classification Search
USPC .................... 62/3.2, 3.3, 3.7, 259.2; 435/283.1–309.4
See application file for complete search history.

(56) References Cited

U.S. PATENT DOCUMENTS

| 5,834,252 | A | 11/1998 | Stemmer et al. |
| 5,882,465 | A | 3/1999 | McReynolds |
| 7,585,663 | B2 * | 9/2009 | Shigeura et al. ........... 435/287.2 |
| 7,665,311 | B2 | 2/2010 | Steffensen et al. |
| 2002/0119535 | A1 | 8/2002 | Slater et al. |
| 2003/0165946 | A1 | 9/2003 | Evans |
| 2005/0282224 | A1 | 12/2005 | Fouillet et al. |

(Continued)

FOREIGN PATENT DOCUMENTS

| WO | WO 2008/070198 | 6/2008 |
| WO | WO 2009/094061 | 7/2009 |
| WO | WO 2010/093249 | 8/2010 |
| WO | WO 2011/028924 | 3/2011 |

OTHER PUBLICATIONS

Amendment filed Oct. 15, 2010 for EP Patent Application No. 08871258.3, filed Nov. 17, 2010.

(Continued)

*Primary Examiner* — Allen Flanigan
*Assistant Examiner* — Antonio R Febles
(74) *Attorney, Agent, or Firm* — Fenwick & West, LLP

(57) ABSTRACT

The rapid thermal cycling of a material is targeted. A solid state heat exchanger with a first well and second well is coupled to a power module. A thermoelectric element is coupled to the first well, the second well, and the power module, is configured to transfer thermal energy from the first well to the second well when current from the power module flows through the thermoelectric element in a first direction, and is configured to transfer thermal energy from the second well to the first well when current from the power module flows through the thermoelectric element in a second direction. A controller may be coupled to the thermoelectric elements, and may switch the direction of current flowing through the thermoelectric element in response to a determination by sensors coupled to the wells that the amount of thermal energy in the wells falls below or exceeds a predetermined threshold.

13 Claims, 7 Drawing Sheets

(56) References Cited

U.S. PATENT DOCUMENTS

| | | | |
|---|---|---|---|
| 2006/0042785 | A1 | 3/2006 | Werner et al. |
| 2006/0094108 | A1 | 5/2006 | Yoder et al. |
| 2008/0022647 | A1 | 1/2008 | Jones et al. |
| 2008/0166793 | A1 | 7/2008 | Beer et al. |
| 2008/0270030 | A1 | 10/2008 | Copley et al. |
| 2009/0226971 | A1 | 9/2009 | Beer et al. |
| 2009/0226972 | A1 | 9/2009 | Beer et al. |
| 2010/0091459 | A1 | 4/2010 | Zhang |
| 2010/0101237 | A1* | 4/2010 | Wu et al. ............... 62/3.2 |

OTHER PUBLICATIONS

Beer, N.R. et al., "On-Chip Single-Copy Real-Time Reverse-Transcription PCR in Isolated Picoliter Droplets," *Anal. Chem.*, 2008, pp. 1854-1858, vol. 80, No. 6.

Beer, N.R. et al., "On-chip, real-time, single-copy polymerase chain reaction in picoliter droplets," Anal. Chem., 2007, pp. 8471-8475, vol. 79.

European Patent Office, Communication Pursuant to Rules 161(1) and 162 EPC, European Patent Application No. 08871258.3, Sep. 8, 2010, two pages.

Finnzymes, Inc., "24-well and 96-well Piko Thermal Cyclers," Jun. 20, 2010, four pages. [Online] [Retrieved Jan. 24, 2012] Retrieved from the Internet <URL:http://web.archive.org/web/20100620081305/http://www.finnzymes.us/Piko/thermalcyclers.html.>.

Fujimoto, T. et al., "Novel High-Speed Real-Time PCR Method (Hyper-PCR): Results from Its Application to Adenovirus Diagnosis," Jpn. J. Infect. Dis., 2010, pp. 31-35, vol. 63.

Griep, M.A. et al., "Kinetics of the DNA Polymerase *Pyrococcus kodakarensis*," Chemical Engineering Science, 2006, pp. 3885-3892, vol. 61.

Khanafer, K. et al.,"Isothermal Surface Production and Regulation for High Heat Flux Applications Utilizing Porous Inserts," *International Journal of Heat and Mass Transfer*, 2001, pp. 2933-2947, vol. 44.

Kim, Y.H. et al., "Performance Evaluation of Thermal Cyclers for PCT in a Rapid Cycling Condition," *BioTechniques*, 2008, pp. 495-505.

Kiss, M. et al., "High-Throughput Quantitative Polymerase Chain Reaction in Picoliter Droplets," *Anal. Chem.*, 2008, pp. 8975-8981, vol. 80, No. 23.

Ksiazek, T. et al.,"A Novel Coronavirus Associated with Severe Acute Respiratory Syndrome," New England Journal of Medicine, 2003, pp. 1953-1966, vol. 348, No. 20.

Lee, W.-G. et al., "Nano/Microfluidics for diagnosis of infectious diseases in developing countries," Advanced Drug Delivery Reviews, 2010, pp. 449-457, vol. 62, No. 4-5.

Mahjoob, S. et al., "Rapid Microfluidic Thermal Cycler for Polymerase Chain Reaction Nucleic Acid Amplification," *International Journal of Heat and Mass Transfer*, 2008, pp. 2109-2122, vol. 51.

Maltezos, G. et al., "Thermal Management in Microfluidics Using Micro-Peltier Junctions," *Applied Physics Letters*, 2005, pp. 154105-1 to 154105-3, vol. 87.

Neuzil, P. et al., "Ultra fast miniaturized real-time PCR: 40 cycles in less than six minutes," Nucleic Acids Res., 2006, vol. 34, No. 11, nine pages.

PCT International Preliminary Report of Patentability, PCT Application No. PCT/US2008/083728, Jul. 27, 2010, seven pages.

PCT International Search Report and Written Opinion, PCT Application No. PCT/US2008/083728, Jun. 2, 2009, ten pages.

Smiths Detection, "Bio-Seeq PLUS: Feature Highlights," 2012, two pages. [Online] [Retrieved Jan. 24, 2012] Retrieved from the Internet <URL:http://www.smithsdetection.com/Bio-Seeq_PLUS.>.

Terazono, H. et al., "Development of a High-Speed Real-Time Polymerase Chain Reaction System Using a Circulating Water-Based Rapid Heat-Exchange," *Japanese Journal of Applied Physics*, Jun. 2010, pp. 06GM05-1 to 06GM05-5, vol. 49, No. 6, Issue 2 of 2.

Tewhey, R. et al., "Microdroplet-based PCR enrichment for large-scale targeted sequencing," *Nature Biotechnology*, Nov. 2009, pp. 1025-1031, vol. 27, No. 11.

U.S. Office Action, U.S. Appl. No. 12/270,348, Jun. 22, 2011, sixteen pages.

U.S. Office Action, U.S. Appl. No. 12/270,030, May 4, 2011, nine pages.

U.S. Office Action, U.S. Appl. No. 12/270,030, Nov. 16, 2011, seven pages.

Wang, Y. et al., "A Novel Strategy to Engineer DNA Polymerases for Enhanced Processivity and Improved Performance in Vitro," *Nucleic Acids Res.*, 2004, pp. 1197-1207, vol. 32, No. 3.

Zhang, C. et al., "Miniaturized PCR chips for nucleic acid amplification and analysis: latest advances and future trends," *Nucleic Acids Research*, 2007, pp. 4223-4237, vol. 35, No. 13.

\* cited by examiner

SOLID STATE RAPID THERMOCYCLING

RELATED APPLICATIONS

This application claims the benefit of U.S. Provisional Application No. 61/390,383, filed Oct. 6, 2010, U.S. Provisional Application No. 61/390,415, filed Oct. 6, 2010, U.S. Provisional Application No. 61/390,425, filed Oct. 6, 2010, U.S. Provisional Application No. 61/390,433, filed Oct. 10, 2010, U.S. Provisional Application No. 61/390,441, filed Oct. 6, 2010, U.S. Provisional Application No. 61/390,452, filed Oct. 6, 2010, and U.S. Provisional Application No. 61/512,393, filed Jul. 27, 2011, the content of which is incorporated by reference herein in its entirety.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The exemplary embodiments relate to thermal cycling and more particularly to a rapid solid state thermal cycler.

BACKGROUND OF THE INVENTION

PCR is the gold standard for fast and efficient nucleic acid analysis. It is the best method for genetic analysis, forensics, sequencing, and other critical applications because it is unsurpassed in specificity and sensitivity. By its very nature the method utilizes an exponential increase in signal, allowing detection of even single-copy nucleic acids in complex, real environments. Accordingly, PCR systems are ubiquitous, and the market for a faster thermocycling method is significant. Recent advancements in microfluidics allow the miniaturization and high throughput of on-chip processes, but they still lack the speed and thermal precision needed to revolutionize the field. Robotic-based PCR systems are very slow in reaction speed, and utilize heating technologies with much less precision and accuracy. These systems typically couple auto-pipettes with robotic manipulators to measure, mix, and deliver sample and reagents. Accordingly, these systems are complex, expensive, and difficult to miniaturize.

SUMMARY OF THE INVENTION

An apparatus for thermally cycling a material is described. A solid state heat exchanger including a first well and a second well for receiving samples to be thermally cycled is coupled to a power module. The solid state heat exchanger also includes a thermoelectric element coupled to the first well, the second well, and the power module. The thermoelectric element transfers thermal energy from the first well to the second well when current from the power module flows through the thermoelectric element in a first direction. Similarly, the thermoelectric element transfers thermal energy from the second well to the first well when current from the power module flows through the thermoelectric element in a second direction. Thermal energy may be exchanged between samples received in the first well and the second well alternately in this way for a determined number of cycles.

A controller may be coupled to the thermoelectric element to switch the direction of current flowing through the thermoelectric element. Sensors may be coupled to the first and/or second well to determine the amount of thermal energy present in the first and/or second well, and to communicate this determined energy to the controller. In response to a received determined energy falling below a first threshold, the controller may switch the direction of current flowing through the thermoelectric element. Likewise, in response to a received determined energy exceeding a first threshold, the controller may switch the direction of current flowing through the thermoelectric element.

In one embodiment, the solid state heat exchanger includes a first set of wells and a second set of wells, and includes a plurality of thermoelectric elements, each thermoelectric element coupled to a well in the first set of wells and a well in the second set of wells. In this embodiment, the plurality of thermoelectric elements may simultaneously transfer thermal energy from the wells in the first set of wells to the wells in the second set of wells and vice versa. In this embodiment, the wells may be arranged in a two-dimensional rectangular array, such that the wells adjacent to a particular well belong to a different set of wells than the particular well. The solid state heat exchanger may be configured to receive a sample tray for containing the samples to be thermally cycled. The solid state heat exchanger may also be configured to receive surface heaters for heating wells receiving thermal energy from the thermoelectric elements.

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Thermal Cycling System Overview

Figure 1:
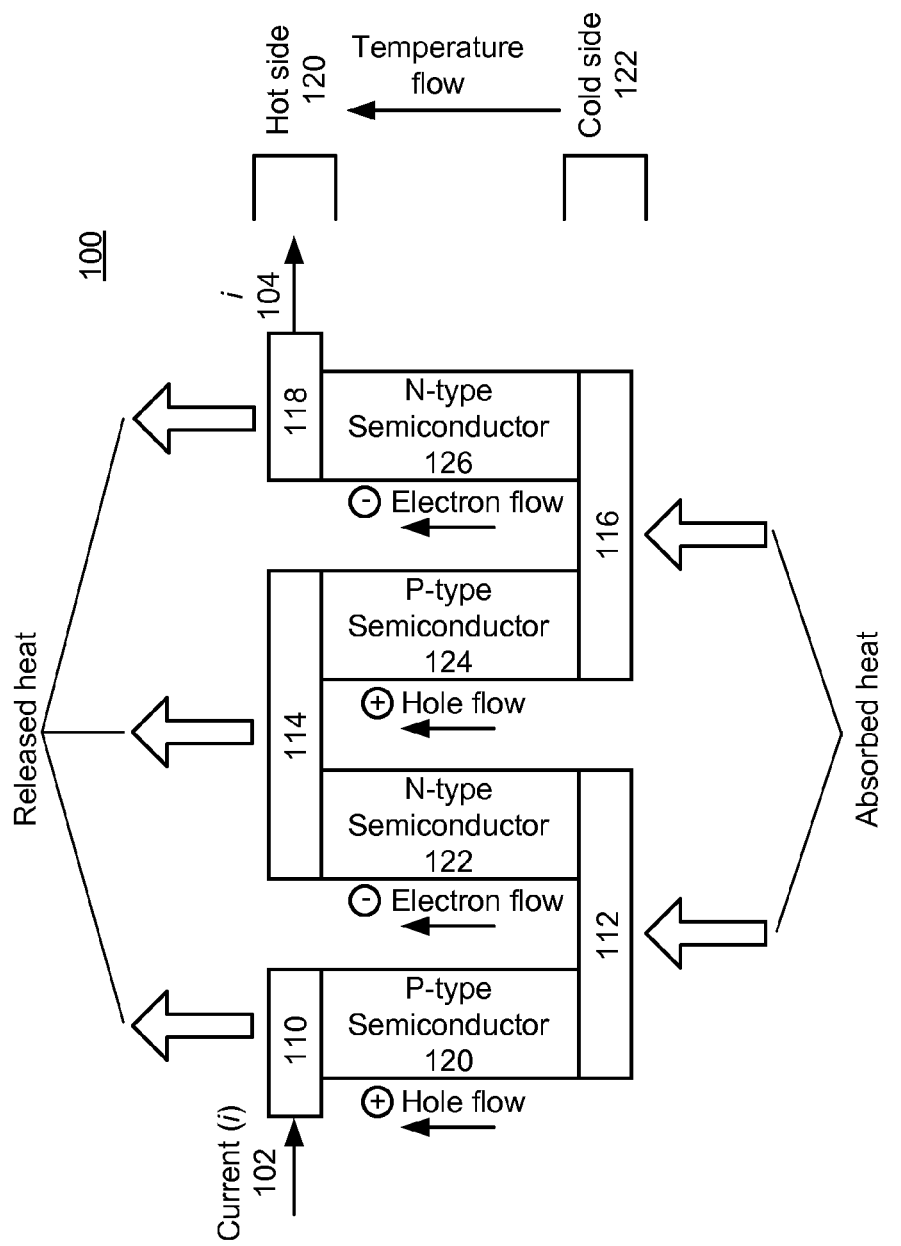
FIG. 1 is an example thermoelectric cooler illustrating the Peltier effect in accordance with one embodiment.

FIG. 1 is an example thermoelectric cooler 100 illustrating the Peltier effect in accordance with one embodiment. The Peltier effect is the presence of thermal energy (hereafter, "heat") at an electrified junction of two different materials. The Peltier effect can be harnessed using a thermoelectric cooler 100 as a heat pump to transfer heat from one location in the cooler 100 to another. Current flows through a thermoelectric cooler 100, causing heat transfer within the cooler 100. By selecting the right materials for the thermoelectric cooler 100, the heat transfer can be coordinated such that the portions of cooler 100 that absorb heat and the portions of the cooler 100 that release heat are co-located, creating a "cold" side (or node) and a "hot" side (or node). It should be noted that although the terms "cold" and "hot" are used, these terms merely refer to relative temperatures. Accordingly, the hot side and the cold side of a thermoelectric cooler 100 may be any temperature such that the temperature of the hot side is greater than the temperature of the cold side.

The thermoelectric cooler 100 includes nodes 110, 112, 114, 116, and 118, connected by semi-conductors 120, 122, 124, and 126. Note that in alternative embodiments, thermoelectric coolers may contain additional or fewer nodes or semiconductors, and the nodes and semiconductors may be configured in a different arrangement. The nodes 110, 112, 114, 116, and 118 may be composed of any material capable of conducting electricity. For example, these nodes may be interconnects made from copper or another metal. The semiconductors 120 and 124 are p-type semiconductors and the semiconductors 122 and 126 are n-type semiconductors. When current flows through p-type semiconductors, positive holes flow in a direction opposite of the current. Likewise, when current flows through n-type semiconductors, electrons flow in the direction of the current. Electrons and positive holes transport heat in the direction of the flow of the electrons and positive holes.

Current (i) 102 flows into the thermoelectric cooler 100 at node 110, through the p-type semiconductor 120 to the node 112, through the n-type semiconductor 122 to the node 114, and so forth until current (i) 104 flows out of the thermoelectric cooler 104 at node 118. Note that the semiconductors 120, 122, 124 and 126 in the thermoelectric cooler 100 are arranged such that the electrons and positive holes flow through the semiconductors 120, 122, 124, and 126 in a uniform direction when current flows through the cooler 100. This arrangement beneficially causes heat to flow through the semiconductors 120, 122, 124, and 126 in a uniform direction.

As heat flows through the semiconductors 120, 122, 124, and 126, heat is moved from one side of each semiconductor towards the other side of the semiconductor. For the semiconductor 120, heat moves from the side in contact with the node 112 towards the side in contact with the node 110. As heat moves from the side of the semiconductor 120 in contact with the node 112, heat is transferred from the node 112 to the semiconductor 120. Likewise, as heat moves towards the side of the semiconductor 120 in contact with the node 110, heat is transferred from the semiconductor 120 to the node 110. The net effect of this heat transfer due to the heat flow through the semiconductor 120 is a transfer of heat from the node 112 to the node 110. Likewise, the heat flow through the semiconductor 122 causes a transfer of heat from the node 112 to the node 114, the heat flow through the semiconductor 124 causes a transfer of heat from the node 116 to the node 114, and the heat flow through the semiconductor 116 causes a transfer of heat from the node 116 to the node 118.

At a system level, as current flows through the thermoelectric cooler 100 from the node 110 to the node 118, heat flows from the nodes 112 and 116 (which absorb heat, becoming cooler) to the nodes 110, 114, and 118 (which release heat, becoming hotter). The nodes 112 and 116 are located within a close proximity to each other, creating a "cold" side 122 to the thermoelectric cooler 100. The nodes 110, 114, and 118 are located within a close proximity to each other, creating a "hot" side 120.

Note that if the direction of the current flowing through the thermoelectric cooler 100 reverses such that current flows into the node 118 and out of the node 110, the direction of the flow of electrons and positive holes through the semiconductors would reverse, causing heat to flow from the nodes 110, 114, and 118 to the nodes 112 and 116. In such an instance, the side of the thermoelectric cooler 110 including the nodes 110, 114, and 118 would be the cold side and the side including nodes 112 and 116 would be the hot side. Thus, by alternating the direction of the current flow through the thermoelectric cooler 110, the temperature of the opposing sides of the thermoelectric cooler 110 alternates relative to each other.

When current flows through the thermoelectric cooler 100, the transfer of heat from one side of the thermoelectric cooler 100 (for instance, the side including the nodes 110, 114, and 118) to the opposing side of the thermoelectric cooler 100 (for instance, the side including the nodes 112 and 116) is not instantaneous. The amount of time it takes for either side to reach a particular temperature, or for the difference in temperature between the sides to reach a particular threshold, is dependent on many factors, including but not limited to the amount of current flowing through the thermoelectric cooler 100, the materials used to make the nodes or semiconductors, the dimensions of the nodes and semiconductors (for example, the distance between the nodes or the length of each semiconductor), and the current temperature of the nodes.

For the purposes of simplicity, the description of thermoelectric coolers hereafter is limited to a hot node and a cold node, or is limited to a thermoelectric element with a hot side and a cold side. In these instances, the thermoelectric cooler 100 of FIG. 1 may be implemented such that the hot side 120 and the cold side 122 of the thermoelectric cooler 100 correlate to the hot node and cold node or hot side and cold side of the described thermoelectric coolers. A description of a thermoelectric cooler with a hot node and a cool node or of a thermoelectric element with a hot side and a cold side is referred to herein as a "thermoelectric element".

Figure 2A:
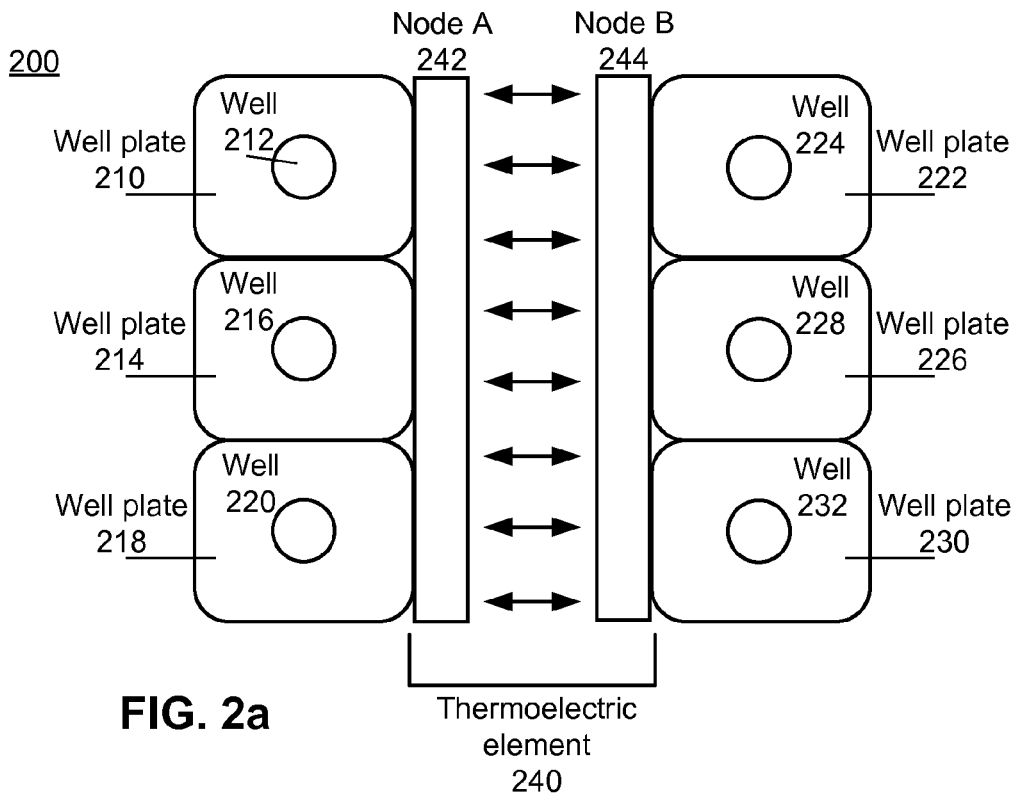
FIG. 2a illustrates a top view of a solid state heat exchanger in a thermal cycling system with a single thermoelectric element in accordance with one embodiment.

FIG. 2a illustrates a top view of a solid state heat exchanger 200 in a thermal cycling system with a single thermoelectric element in accordance with one embodiment. The solid state heat exchanger 200 of the embodiment of FIG. 2a includes exchanger wells 212, 216, 220, 224, 228, and 232, each in a well plate 210, 214, 218, 222, 226, and 230, respectively. The solid state heat exchanger 200 is configured to receive one or more samples to be thermally cycled in the wells. The solid state heat exchanger 200 also includes a thermoelectric element 240 with a node A 242 and a node B 244. The solid state heat exchanger 200 is configured to cycle the received samples between a first temperature (T1) and a second temperature (T2) using the thermoelectric element 240. In alternative embodiments, the solid state heat exchanger 200 may include fewer or additional wells and well plates, the wells and well plates may be any size or shape, and the wells and well plates may be configured differently. Likewise, in alternative embodiment, the solid state heat exchanger 200 is configured to cycle the received samples between more than two temperatures.

The thermoelectric element 240 may be composed of any materials capable of transferring heat when current flows through the thermoelectric element 240. In one embodiment, the thermoelectric element 240 may be fabricated on a thermally insulating substrate. For example, the thermoelectric element 240 may be fabricated on alumina, zirconia, or any other ceramic/oxide material or polymer. Such an embodiment mitigates heat loss and improves the heat transfer efficiency of the thermoelectric element 240.

In one embodiment, the exchanger wells 212, 216, 220, 224, 228, and 232 are configured to directly receive and contain samples to be thermally cycled. Alternatively, the exchanger wells may be configured to receive a sample tray containing samples to be thermally cycled. In such an embodiment, the exchanger wells may be arranged to receive a similarly arranged sample tray such that the wells of the sample tray fit into the exchanger wells. Such an embodiment will be discussed in greater detail in FIGS. 5-6. The size and geometry of the exchanger wells 110 may be designed in order to accommodate the diffusion time requirements of PCR. For example, the surface area of the exchanger wells may be maximized relative to the volume of the exchanger wells, subject to the feasibility of manufacturing constraints. In one embodiment, the exchanger wells are configured to receive and contain samples of 1-10 µL, 3-7 µL or approximately 5 µL. It is not strictly necessary for all wells to be configured identically, provided that they accommodate a sample holder, if used with a sample holder.

The well plates may be composed of any material, though optimally the well plates are composed of thermally conductive materials, such as aluminum or copper. Polymer films may also be used, as the width of such films may be minimized, increasing the rate and efficiency of heat transfer. As current flows through the thermoelectric element 240 and heat flows between node A 242 and node B 244, heat is transferred between the first set of well plates 210, 214, and 218 and the second set of well plates 222, 226, and 230. For example, if current flows through the thermoelectric element 240 such that heat flows from node A 242 to node B 244, heat flows from the first set of well plates into node A 242, and heat flows from node B 244 into the second set of well plates. Thus, heat flows from the first set of wells plates to the second set of well plates. If the current flows through the thermoelectric element 240 in the opposite direction, heat flows from the second set of well plates to the first set of well plates. The amount of thermal energy in the well plates is transferred to samples contained in the wells. Alternating the direction of current flowing through the thermoelectric element 240 alternates the temperature of the sets of well plates and likewise alternates the temperature of the samples contained in the wells.

Figure 2B:
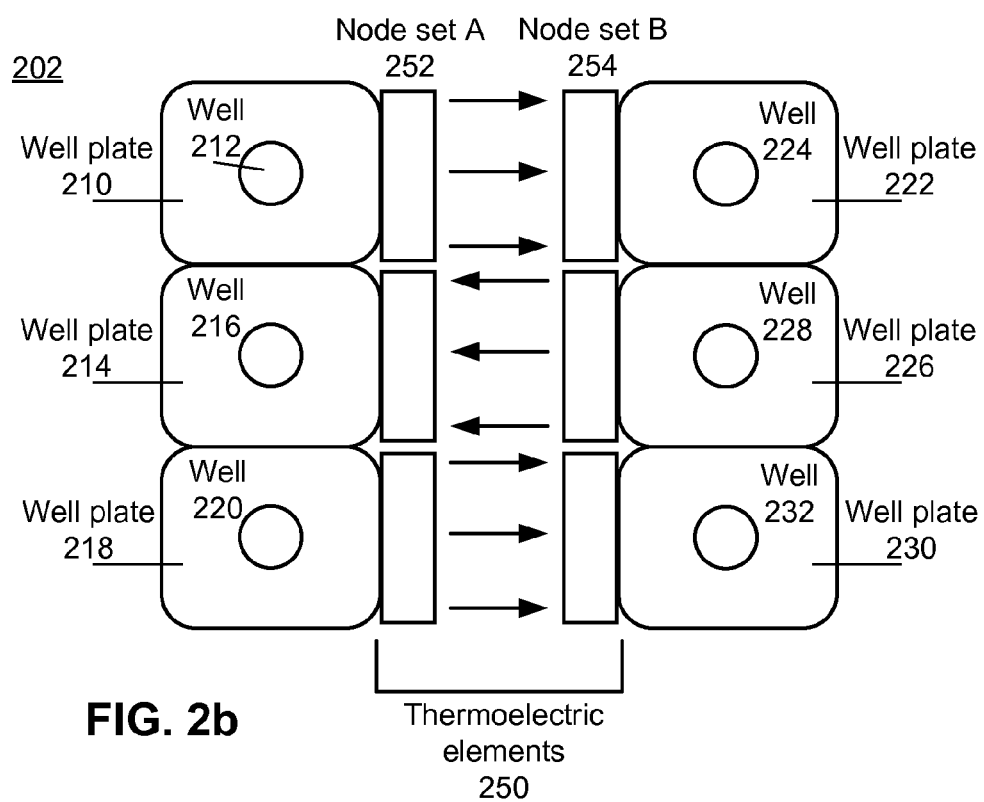
FIG. 2b illustrates a top view of a solid state heat exchanger in a thermal cycling system with a thermoelectric element for each heat exchanger well pair in accordance with one embodiment.

FIG. 2b illustrates a top view of a solid state heat exchanger 200 in a thermal cycling system with a thermoelectric element for each heat exchanger well pair in accordance with one embodiment. The embodiment of FIG. 2b includes three heat exchanger well pairs, one for each of wells 212 and 224, wells 216 and 228, and wells 220 and 232, and each well pair includes a thermoelectric element. In the embodiment of FIG. 2b, the samples in the wells of a well pair may be thermally cycled independently of the samples in the wells of the other well pairs. As illustrated in FIG. 2b, heat is flowing from the well plate 210 to the well plate 222, heat is flowing from the well plate 226 to the well plate 214, and heat is flowing from the well plate 218 to the well plate 230.

In the embodiment of FIG. 2a, the thermal conductivity of adjacent well plates may be maximized in order to increase the efficiency of heat transfer from the first well plate set to the second well plate set. In the embodiment of FIG. 2b, the thermal conductivity of adjacent well plates may be minimized (using, for instance, insulation) in order to thermally isolate each heat exchanger well pair, allowing the thermal cycling of each heat exchanger well pair to operate independently of each other well pair and increasing the efficiency of heat transfer within each well pair.

The thermoelectric elements 240 or 250 may be arranged in a planar orientation, or may be arranged in any other suitable geometry. The thermoelectric elements 240 and 250 may be created using, for example, microfabrication or thin-film deposition techniques. The thermoelectric elements 240 and 250 may also be photolithographically etched onto a substrate in a solid state fashion. Any suitable method for implementing the thermoelectric elements 240 and 250 (or any other thermoelectric element arrangement discussed herein) may be used.

Figure 3A:
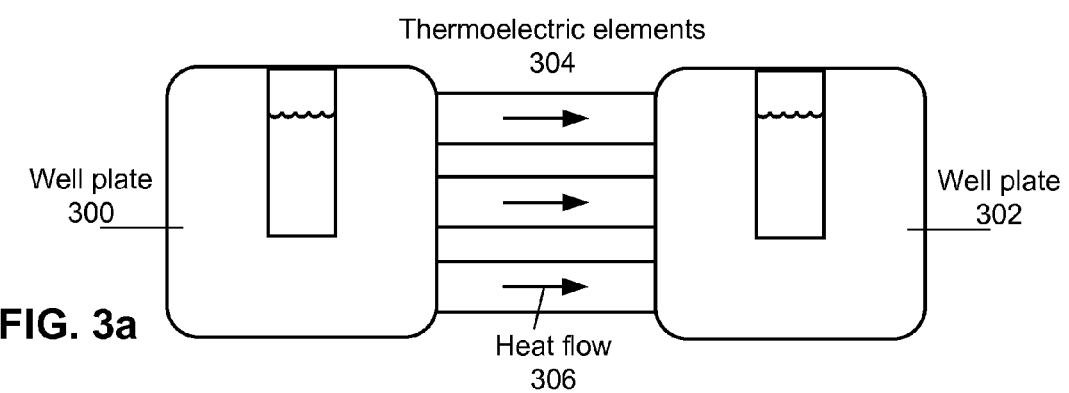
FIG. 3a illustrates a side view of a solid state heat exchanger well pair with multiple thermoelectric elements with heat flowing in a first direction in accordance with one embodiment.
Figure 3B:
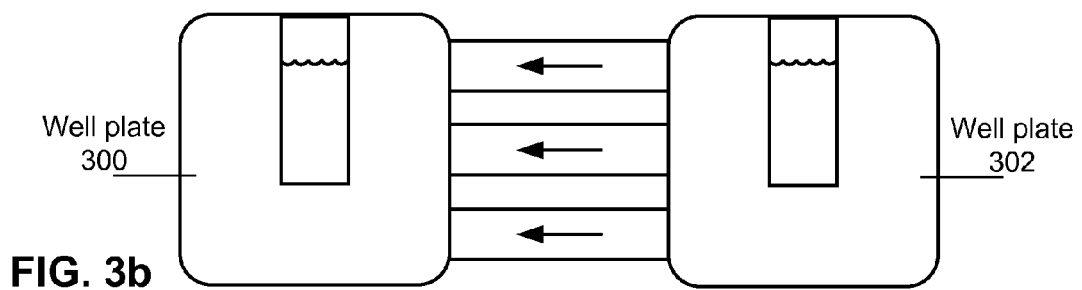
FIG. 3b illustrates a side view of a solid state heat exchanger well pair with multiple thermoelectric elements with heat flowing in a second direction in accordance with one embodiment.

As discussed above, the solid state heat exchanger 200 is configured to thermally cycle samples contained in the exchanger wells by iteratively alternating the flow of heat between heat exchanger wells. FIG. 3a illustrates a side view of a solid state heat exchanger well pair with multiple thermoelectric elements with heat flowing in a first direction in accordance with one embodiment. In this embodiment, multiple thermoelectric elements 304 are arranged vertically between the well plate 300 and the well plate 302 and the thermoelectric elements 304 are causing heat to flow from the well plate 300 to the well plate 302. FIG. 3b illustrates a side view of a solid state heat exchanger well pair with multiple thermoelectric elements with heat flowing in a second direction in accordance with one embodiment. In this embodiment, the thermoelectric elements 304 are causing heat to flow from the well plate 302 to the well plate 300. In one embodiment, the solid state heat exchanger 200 iteratively alternatives the flow of heat between wells for a set amount of time or for a set number of iterations.

Figure 4A:
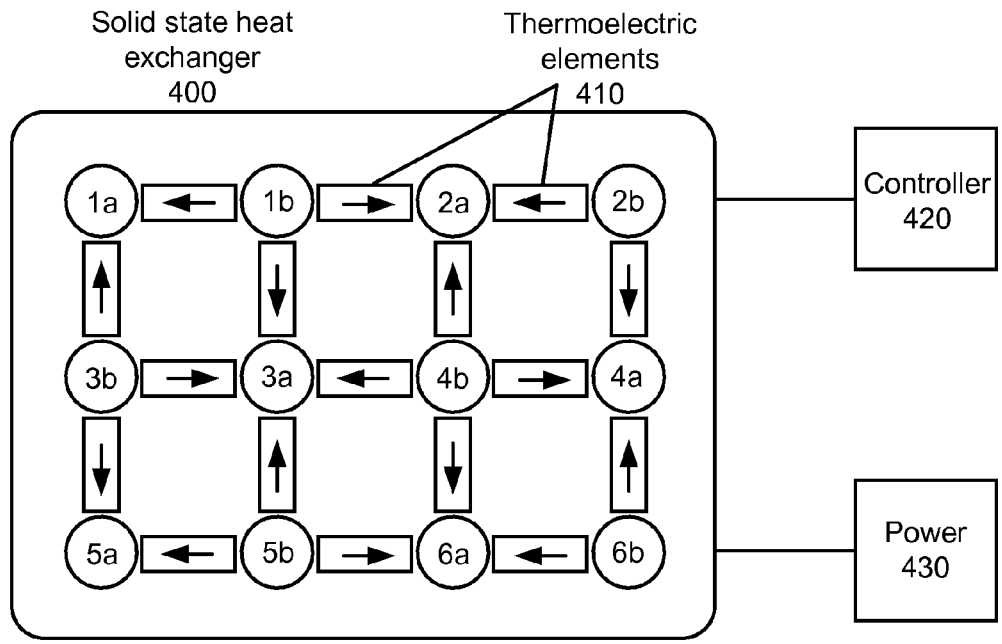
FIG. 4a illustrates a solid state heat exchanger in a thermal cycling system in a first cycling phase in accordance with one embodiment.
Figure 4B:
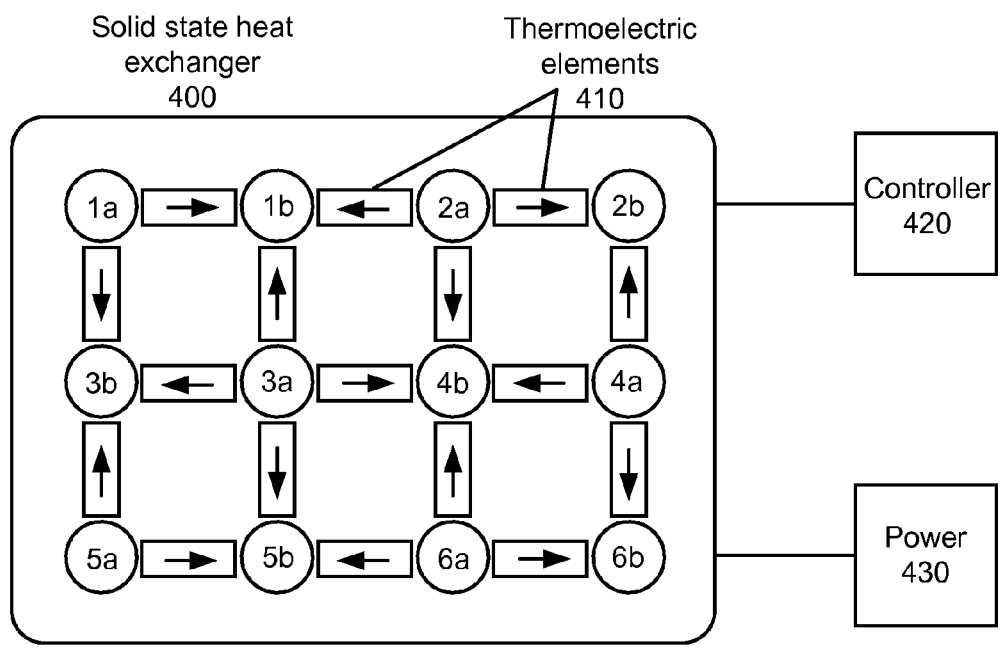
FIG. 4b illustrates a solid state heat exchanger in a thermal cycling system in a second cycling phase in accordance with one embodiment.

FIG. 4a illustrates a solid state heat exchanger in a thermal cycling system in a first cycling phase in accordance with one embodiment. FIG. 4b illustrates a solid state heat exchanger in a thermal cycling system in a second cycling phase in accordance with one embodiment. In the embodiments of FIG. 4a and FIG. 4b, the solid state heat exchanger 400 includes 12 exchanger wells (labeled 1a through 6b) in a 4-by-3 two-dimensional array. In alternative embodiments, the solid state heat exchanger 400 includes fewer or additional wells, and the array of wells may be configured differently. The distance between the wells may be minimized in order to increase the efficiency of heat transfer between the wells. In one embodiment, each well may be 3 cm or less away from one or more adjacent wells. Between vertically and horizontally adjacent wells in the solid state heat exchanger 400 are thermoelectric elements 410 configured to transfer heat between wells. Although not illustrated in FIGS. 4a and 4b, each of the 12 wells may be contained in a dedicated thermally conductive well plate. Alternatively, the thermoelectric elements 410 may transfer heat directly between the wells.

The solid state heat exchanger 400 may additionally include a controller 420 (described below in greater detail) and a power module 430. The power module 430 may be any system capable of providing power to the solid state heat exchanger 400. For example, the power module 430 may include one or more batteries or capacitors, a power generator, or a utility power provider. The controller 420 uses power from the power module 430 to provide current to the thermoelectric elements 410 in order to transfer heat between wells.

The embodiment of FIGS. 4a and 4b is configured such that heat is exchanged between two sets of wells iteratively in 2 phases. The first set of wells includes wells 1a, 2a, 3a, 4a, 5a, and 6a, and the second set of wells includes wells 1b, 2b, 3b, 4b, 5b, and 6b. In the first phase, heat is transferred from the second set of wells to the first set of wells. In the second phase, heat is transferred from the first set of wells to the second set of wells. When in the first phase, the thermoelectric elements 410 adjacent to each well in the second set of wells are configured to transfer heat from the well to the wells adjacent to the well. For example, the thermoelectric elements 410 surrounding well 4b are configured to transfer heat from well 4b to the adjacent wells 2a, 3a, 4a, and 6a. Likewise, when in the second phase, the thermoelectric elements 410 adjacent to each well in the first set of wells are configured to transfer heat from the well to the wells adjacent to the well. For example, the thermoelectric elements 410 surrounding well 2a are configured to transfer heat from well 2a to the adjacent wells 1b, 2b, and 4b. Thus, heat oscillates between the first and second sets of wells, causing the temperature of the samples in each set of wells to iteratively increase and decrease.

The embodiment of FIGS. 4a and 4b beneficially allows heat to be preserved within the solid state heat exchanger 400 by transferring the heat between wells during thermal cycling. By transferring heat between wells, less energy is required to produce heat to transfer to the wells, increasing the efficiency of the solid state heat exchanger 400. In order to further increase efficiency, the solid state heat exchanger 400 may be thermally insulated such that external heat loss is minimized. Further, each individual well in the solid state heat exchanger may be thermally insulated to minimize heat loss. In such an embodiment, the well insulation does not prevent the thermoelectric elements 410 adjacent to the wells from transferring heat to and from the wells.

Although not illustrated in the embodiment of FIGS. 4a and 4b, the solid state heat exchanger 400 may additionally include sensors to monitor the temperature of the wells or the samples in the wells, the efficiency of the thermoelectric elements 410, the rate of heat transfer between wells by the thermoelectric elements 410, or any other property related to thermal cycling. The sensors may include thermocouples, thermometers, or thermistors. The sensors may be configured to report this information to the controller 420. Information received from these sensors may allow the controller 420 to dynamically control the thermal cycling of samples in the solid state heat exchanger 400 on a well-by-well basis by individually controlling the current flowing through thermoelectric elements 410.

In one embodiment, the solid state heat exchanger 400 is configured to thermally cycle samples according to the requirements of PCR. In addition, the solid state heat exchanger 400 may be configured to be packaged into a comprehensive PCR system. For example, the solid state heat exchanger 400 may be configured to be covered by a set of optical detectors for real-time measurement of DNA amplification resulting from the thermal cycling of a PCR reagent mix. Further, the controller 420 may be configured to thermally cycle samples contained with the solid state heat exchanger 400 according to the general requirements of PCR, of particular PCR reagents, and of pre-determined PCR parameters of particular experiments.

Solid State Heat Exchanger Controller

The controller 420 of the solid state heat exchanger 400 controls transfer of heat between wells by the thermoelectric elements 410. As discussed above, the controller 420 may be coupled to one or more sensors configured to determine, for example, the amount of thermal energy in the wells or the samples in the wells, the temperature of the wells or the samples in the wells, the efficiency of the thermoelectric elements 410, and the rate of heat transfer between wells by the thermoelectric elements 410. The controller 420 may retrieve power from the power module 430 and may direct current through the thermoelectric elements 410 such that heat flows from one set of wells to the other. After a sample or well temperature is reached, or after a pre-determined amount of time, the controller 420 may switch the direction of current through the thermoelectric elements 410 such that the direction of heat flow between the sets of wells is reversed. Instead of retrieving power from the power module 430, the controller 420 may direct power provided by the power module 430 in such a way that current flows through the thermoelectric elements 410 in the desired direction. Although not illustrated, in certain embodiments, a controller similar to the controller 420 may be implemented in the embodiments of FIGS. 2a, 2b, 3a, and 3b, and the principles described herein apply equally to these embodiments.

The controller 420 may direct current through the thermoelectric elements 410 in response to a user initiating a thermal cycling operation. Likewise, the controller 420 may stop current flowing through the thermoelectric elements 410 in response to a determination to end a thermal cycling operation, based on, for example, user input, the passage of a pre-determined threshold of time, the cycling of a pre-determined number of cycles, or any other factors indicating the end of a thermal cycling operation. For simplicity, the remainder of this description will be limited to embodiments where the controller 420 operates based on the determined thermal energy (temperature) of the samples, though in other embodiments, the controller 420 may operate based on the determined temperature of the wells, the amount of time passed between oscillations, the efficiency of the thermoelectric elements, etc.

The switching of the direction of the current flowing through the thermoelectric elements 410 twice is referred to herein as a "thermal cycle". In one thermal cycle, heat flows into each well in a first set of wells from a second set of wells in a first phase, and heat flows into each well in the second set of wells from the first set of wells in a second phase. The controller 420 may oscillate the samples contained in the wells of the solid state heat exchanger 400 through a pre-determined number of cycles. For example, the controller 420 may oscillate the samples between 30 and 35 times. Oscillating the samples through a pre-determined number of cycles, for a pre-determined amount of time, or until some other pre-determined metric is met is referred to herein as performing an experiment.

The controller 420 may determine (via one or more temperature sensors) that the temperature of samples in either set of wells falls below a first threshold (T3). In response to such a determination, the controller 420 may switch the direction of the current flowing through the thermoelectric elements 410. Likewise, if the controller 420 determines that the temperature of samples in either set of wells exceeds a second threshold (T4), the controller 420 may also switch the direction of the current flowing through the thermoelectric elements 410.

The first and second controller temperature thresholds T3 and T4 may be pre-determined. In one embodiment, T3 and T4 are determined to be within a pre-determined number of degrees (for instance, degrees Kelvin) of T1 and T2 (the temperatures between which the samples are to be cycled). Alternatively, T3 and T4 may be determined based on the requirements of the PCR reaction or on the samples to be thermally cycled. Generally, T3 represents a temperature greater than the temperature represented by T1 and T4 represents a temperature less than the temperature represented by T2, such that T1<T3<T4<T2. In one example embodiment, T1 is between 51° C. and 59° C., T2 is between 93° C. and 98° C., T3 is between 60° C. and 65° C., and T4 is between 87° C. and 92° C.

In one embodiment, the solid state heat exchanger 400 utilizes bias heating to maintain the solid state heat exchanger 400 at a bias temperature. For example, the solid state heat exchanger 400 may utilize a bias temperature of 50° C. In one embodiment, the solid state heat exchanger 400 utilizes bias cooling. For example, the solid state heat exchanger 400 may utilize a heat sink with a speed-controllable fan to implement bias cooling. In one embodiment, the parameters of the bias heating and bias cooling are dependent on the requirements of PCR. The bias heating and bias cooling may be implemented using the thermoelectric elements described herein, or using the surface heaters described below.

It should be noted that even after the controller 420 switches the direction of current flowing through the thermoelectric elements 410, the temperature of the samples may continue to rise and fall past the thresholds T3 and T4 due to the lag between switching current directions, the lag between switching heat flow direction through the thermoelectric elements 410, and the heat transfer between the wells and the samples due to the residual heat in the wells and/or well plates. Accordingly, the thresholds T3 and T4 may be selected to account for these delays. For example, the amount of rise or fall in temperature of the samples after the direction of the current flowing through the thermoelectric elements 410 is switched may be determined, and this amount may be added to T1 or subtracted from T2 in order to determine T3 and T4, respectively.

In one embodiment, the controller 420 may determine T3 and T4 in real-time. For example, the controller 420 may determine that, in response to switching the direction of current flowing through the thermoelectric elements 410 when the samples in a set of wells reach T3, the temperature of the samples does not quite reach T1. In this instance, the controller 420 may decrease T3 for subsequent cycles. Likewise, the controller 420 may increase T4 in response to a determination that the temperature of the samples in the set of wells does not quite reach T2. In one embodiment, the controller 420 utilizes proportional error calculations to determine temperature switching thresholds. In one embodiment, the controller 420 utilizes proportional integral derivative (PID) control schemes to accommodate higher fluid temperatures or tighter temperature tolerances.

The controller 420 may store successful threshold values (the temperature thresholds T3 and T4 that produce the desired sample temperatures T1 and T2 with an acceptable margin of error, respectively) in a parameters database. Further, the controller 420 may store the time intervals between switching the direction of current flowing through the thermoelectric elements 410, the number of cycles performed in a particular experiment, or any other relevant parameters (such as parameters related to the application of surface heaters discussed below). The stored thresholds, temperatures and other parameters (referred to herein collectively as the "experiment parameters") may be stored in conjunction with the experiment type and the sample type associated with the stored parameters. When a new experiment is being performed by the solid state heat exchanger 400, the controller 420 may query the parameters database to retrieve parameters for previously performed experiments similar to the new experiment.

In one embodiment, the controller 420 switches the direction of current flowing through the thermoelectric elements 410 after the passage of a pre-determined amount of time, independently of the temperature of the samples in the wells. For example, the controller 420 may switch the direction of current flowing through the thermoelectric elements 410 approximately every 1.5 seconds. Alternatively, the controller 420 may switch the direction of current flowing through the thermoelectric elements 410 after the controller 420 first detects that the temperature of the samples in either set of wells has exceeded or fallen below a particular threshold and then after a pre-determined amount of time has passed. In this embodiment, the samples are held above or below the particular threshold for a guaranteed amount of time before the direction of current flowing through the thermoelectric elements.

Figure 7:
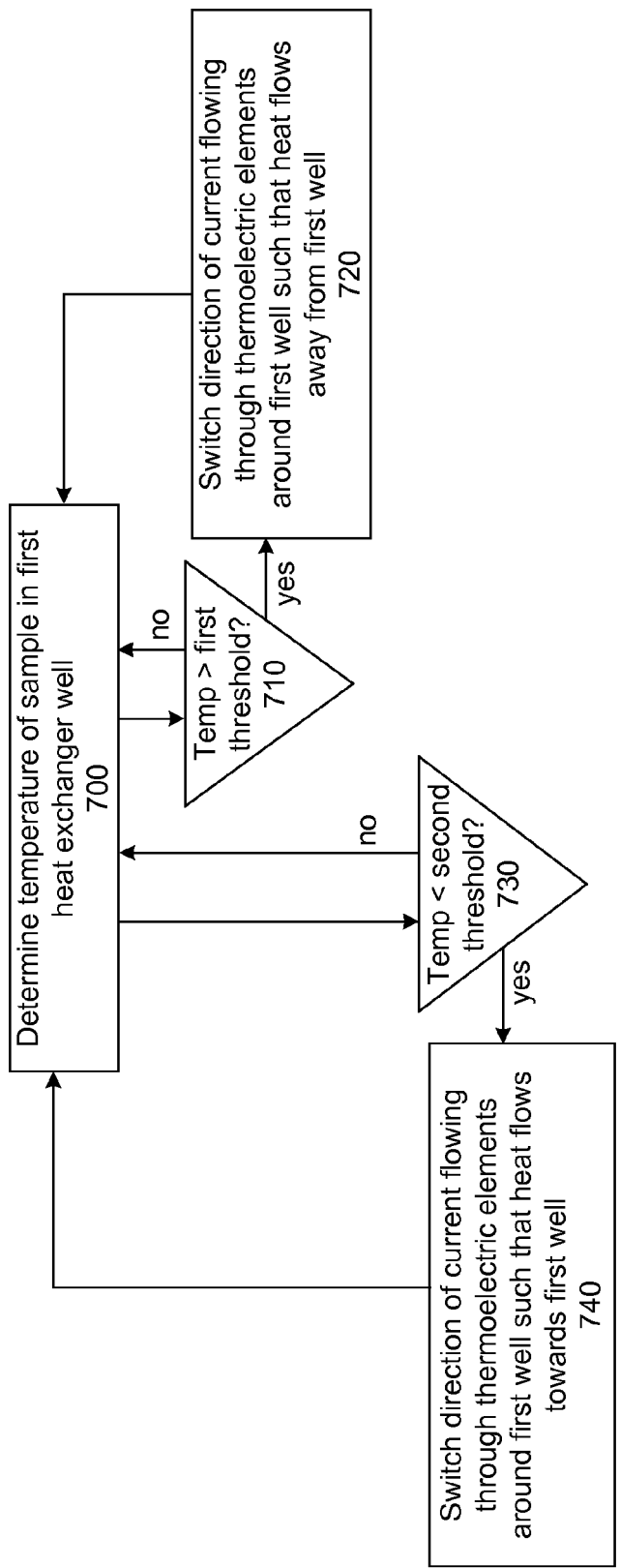
FIG. 7 is a flowchart illustrating the thermal cycling of a sample in a solid state heat exchanger in accordance with one embodiment.

FIG. 7 is a flowchart illustrating the thermal cycling of a sample in a solid state heat exchanger in accordance with one embodiment. The temperature of a sample in one or more solid state heat exchanger wells is determined 700. As discussed above, instead of determining the temperature of the sample itself, the temperature of the walls of the exchanger wells or the temperature of the porous medium in the solid state heat exchanger may be determined and used for the purpose of thermal cycling temperature thresholds. Likewise, the temperatures of all wells in a set of wells may be determined, or the average temperature of wells in a set of wells may be determined. If the determined temperature exceeds 710 a first threshold, the direction of current flowing through the thermoelectric elements around the first well, or around the first set of wells, is switched 720, such that the thermoelectric elements cause heat to flow away from the first well or first set of wells. If the determined temperature falls below 730 a second threshold, the direction of current flowing through the thermoelectric elements around the first well, or around the first set of wells, is switched 730, such that the thermoelectric elements cause heat to flow towards the first well or first set of wells. This process may repeat for a set number of iterations, or for a set amount of time.

Thermal Cycling System Sample Tray

Figure 5:
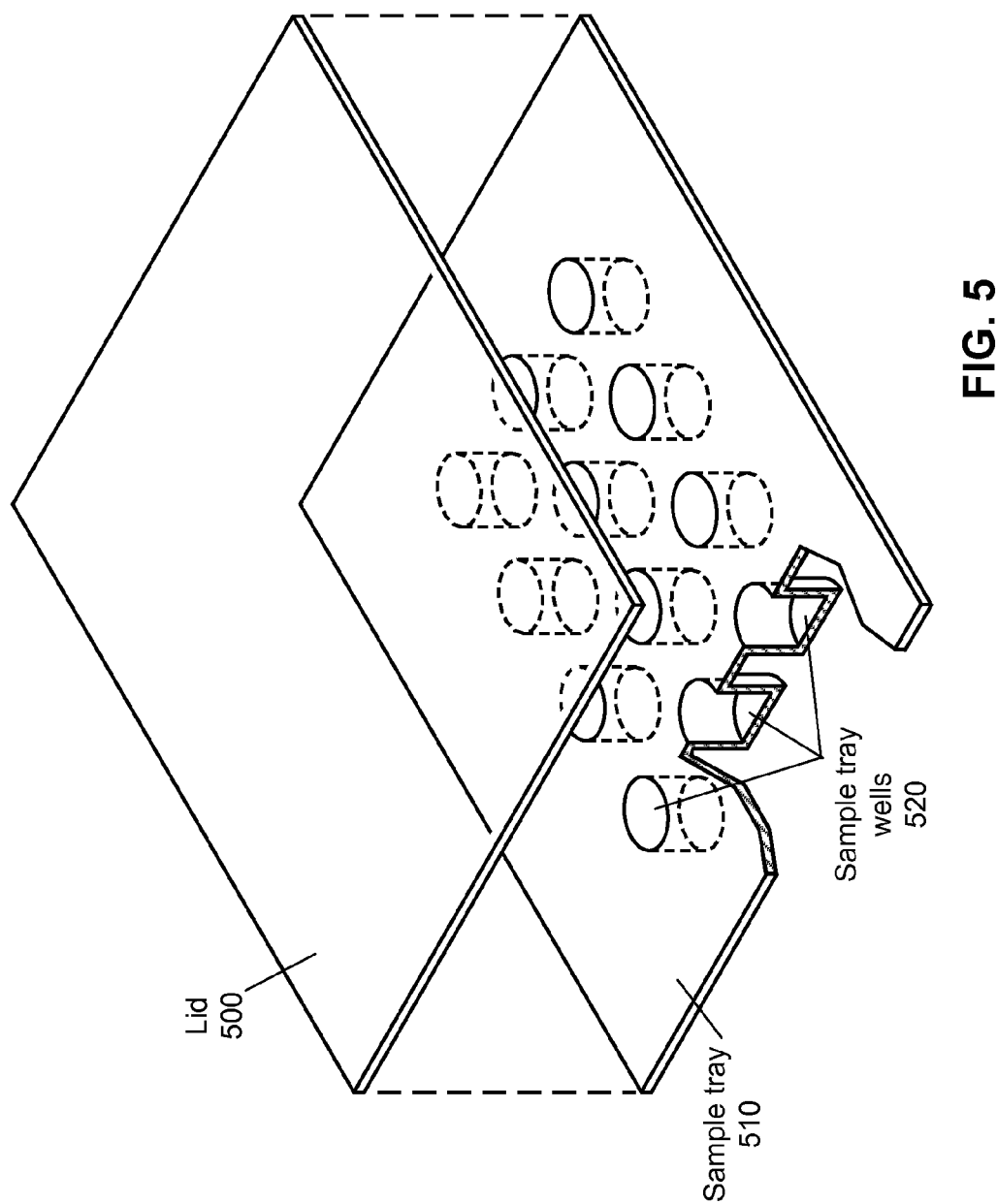
FIG. 5 illustrates a perspective view of a sealable sample tray and tray lid in accordance with one embodiment.

FIG. 5 illustrates a perspective view of a sealable sample tray and tray lid in accordance with one embodiment. The sealable sample tray is configured to allow a user to load samples to be thermally cycled into the sealable sample tray, and to allow a user to thermally cycle the samples loaded into the sample tray using the solid state heat exchangers described herein, for example in the embodiments of FIGS. 2, 3, and 4.

The embodiment of FIG. 5 includes a lid 500 and a sample tray 510. The lid 500 and sample tray 500 may be made of any material, for instance a polymer film (such as polypropylene), aluminum, copper, silicon, or any other suitable material. In one embodiment, the lid 500 and sample tray 510 are made of a highly thermally conductive material to aid in thermal cycling. Alternatively, the lid 500 and sample tray 510 may be made of a poorly thermally conductive material, but may be made extremely thin such that the heat exchange distance is minimized to compensate for the poor conductivity of the material. The lid 500 and the sample tray 510 may be made of an optically transparent material such that the fluorescence of samples can be monitored throughout the thermal cycling process, providing a user with the ability to conduct real-time assays with samples.

In one embodiment, the sample tray 510 includes sample tray wells 520 for inserting and containing samples to be thermally cycled. The sample tray wells 520 may be of any size, shape or configuration, and although 12 wells are displayed in the embodiment of FIG. 5, the sample tray 510 may contain any number of sample tray wells 520. In one embodiment, the size, shape, configuration and number of sample tray wells 520 are configured based on the size, shape, configuration and number of solid state heat exchanger wells, such that the sample tray 510, when placed upon the solid state heat exchanger, results in the sample tray wells 520 aligning with the exchanger wells. In such an embodiment, the contact between the outer surface of the sample tray wells 520 and the inner surface of the exchanger wells is maximized, aiding the thermal cycling of samples to be thermally cycled.

The shape of the sample tray wells 520 may be hemispherical, such that the distance of thermal diffusion into or out of the wells is constant from all sides of the wells to the center of the sample contained within the wells. The shape of the sample tray wells 520 may be conical, such that the surfaces of the wells are more rigid and less likely to deform during thermal cycling. The shape of the sample tray wells 520 may be cylindrical, such that the largest sample volume for a constant cross-sectional area may be thermally cycled. The shape of the sample tray wells 520 may also be a morphology of hemispherical, conical, cylindrical, and/or any other geometric configuration.

The lid 500 is configured to attach or seal to the sample tray 510. The lid 500 may be configured to seal each individual sample tray well 520 such that the sample tray well 520, when sealed, is air tight. In one embodiment, the lid 500 and the sample tray 510 seal using an adhesive liner on the lid 500 or the sample tray 510. The adhesive liner may be configured in any arrangement on the lid 500 or the sample tray 510. In one embodiment, adhesive liner is applied around the top edge of each sample tray well 520, sealing each sample tray well 520 individually when the lid 500 is sealed to the sample tray 510. The lid 500 may include a removable adhesive backing which protects an adhesive liner on the lid 500 until the removable adhesive backing is removed. In this embodiment, in order to apply and seal the lid 500 to the sample tray 510, a user must remove the removable adhesive backing such that the adhesive liner of the lid 500 is exposed, and place the lid 500 on the sample tray 510 such that the adhesive liner of the lid 500 adheres to the sample tray 510.

In one embodiment, the lid 500 and the sample tray 510 are resealable, allowing for multiple uses using the sample lid 500 and sample tray 510. Alternatively, the lid 500 and the sample tray 510 may be sealable only once, resulting in a disposable sample tray 510. In one embodiment, channels may be etched into the sample tray 510. In this embodiment, after the lid 500 is sealed to the sample tray 510, a vacuum may be applied to the channels to remove the air from within each sealed sample tray well 520.

In one embodiment, the sample tray wells 520 are pre-filled with reagents, e.g., reagents for a PCR reaction, and the lid 500 is pre-sealed to the sample tray 510 in order to prevent the reagents within the sample tray wells 520 from leaking. In such an embodiment, a user may remove the lid 500, may insert one or more samples to be thermally cycled into the reagents in the sample tray wells 520, and may re-seal the lid 500 onto the sample tray 510.

Once a thermal cycling process is complete, a user may remove the sample tray 510 from the solid state heat exchanger 105 so that the thermally cycled samples may be analyzed. In one embodiment, the thermally cycled samples may be analyzed by removing the lid 500 from the sample tray 510, and extracting the samples from the sample tray wells 520. Alternatively, the thermally cycled samples may be extracted by piercing the lid 500 using, for example, a hypodermic needle, and removing the thermally cycled samples with the hypodermic needle.

Figure 6A:
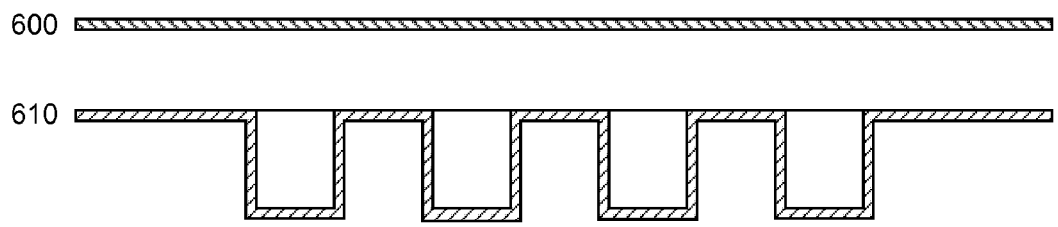
FIG. 6a illustrates a cutaway side view of an unsealed sample tray and tray lid in accordance with one embodiment.
Figure 6B:
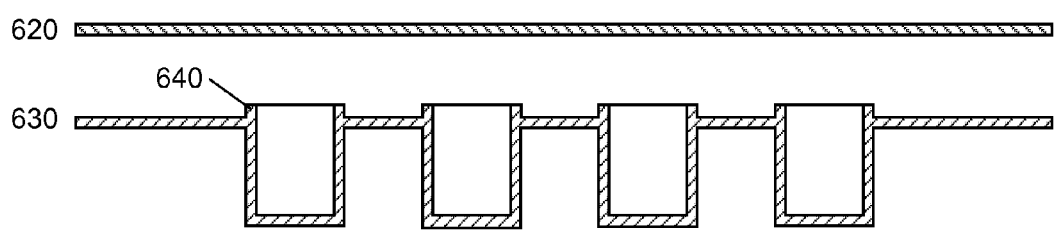
FIG. 6b illustrates a cutaway side view of an unsealed sample tray with protruding sample well ridges and tray lid in accordance with one embodiment.

FIG. 6a illustrates a cutaway side view of an unsealed sample tray and tray lid in accordance with one embodiment. In this embodiment, the lid 600 is not sealed to the sample tray 610. FIG. 6b illustrates a cutaway side view of an unsealed sample tray with protruding sample well ridges and tray lid in accordance with one embodiment. In this embodiment, the lid 620 is not sealed to the sample tray 630. The sample tray 630 contains ridges 640 around the top edge of each sample well. The ridges beneficially help form a seal with the lid 620 when the lid 620 is sealed to the sample tray 630.

Figure 6C:
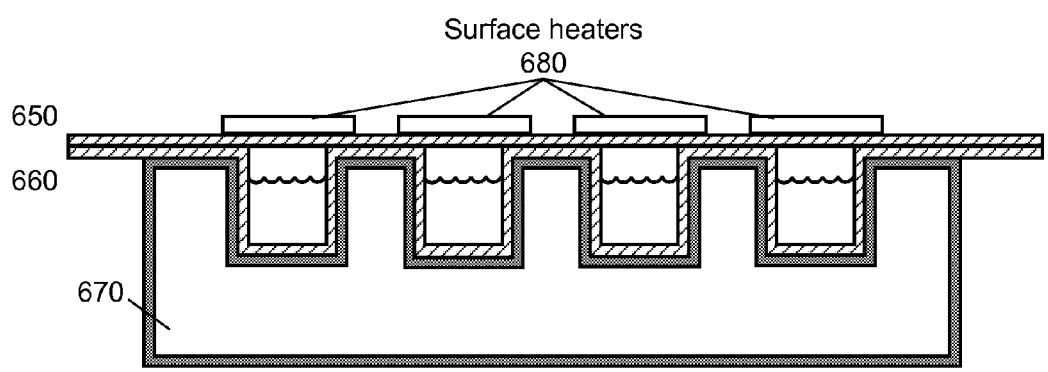
FIG. 6c illustrates a cutaway side view of a sealed sample tray and tray lid placed upon a solid state heat exchanger with surface heaters in accordance with one embodiment.

FIG. 6c illustrates a cutaway side view of a sealed sample tray and tray lid placed upon a solid state heat exchanger with surface heaters in accordance with one embodiment. In this embodiment, the lid 650 is sealed to the sample tray 660 using, for example, an adhesive sealant. Further, in this embodiment, the sample tray 660 and sealed tray lid 650 has been placed upon the solid state heat exchanger 670 such that the sample tray wells are inserted into the heat exchanger wells.

In the embodiment of FIG. 6c, surface heaters 680 have been placed upon the sample tray 660 and sealed tray lid 650 such that the surface heaters 680 are able to heat the sample tray wells and samples from above the sample tray 650. The surface heaters 680 may be used to complement the heating of samples in the set of wells which the thermoelectric elements are transferring heat to in each cycling phase. The surface heaters 680 may be integrated or embedded into the top surface of the solid state heat exchanger 670, may be embedded or integrated into the walls of the exchanger wells, or may be placed on top of a sample tray 660 placed upon the solid state heat exchanger.

The surface heaters 680 may include electrical filament, wiring, resistive tape, or any other material which produces heat from electrical current. Alternatively, other types of surface heaters 680 may also be used. Each well may have an associated surface heater 680. Alternatively, the surface heaters 680 may form a single conduit which encircles each set of wells, allowing a single electrical current to be run through the conduit, heating each set of wells simultaneously and independently, and allowing for the unobstructed optical monitoring of the fluorescence of samples throughout the thermal cycling process from above the sample tray wells.

In one embodiment, the controller 420 controls the activation of the surface heaters 680. The controller 420 may synchronize the switching of the direction of current through the thermoelectric elements with the activation and deactivation of the surface heaters 680. For example, when the controller 420 switches the direction of the current through the thermoelectric elements such that heat flows into a well or a set of wells, the controller 420 may activate the surface heaters 680 associated with the well or set of wells. Likewise, when the controller 420 switches the direction of the current through the thermoelectric elements such that heat flows away from a well or a set of wells, the controller 420 may deactivate the surface heaters 680 associated with the well or set of wells. In one embodiment, the controller 420 staggers the activation and deactivation of the surface heaters 680 with the switching of direction of current flowing through the thermoelectric elements.

In one embodiment, the controller 420 utilizes cascaded PID controllers in conjunction with tape heater surface heaters to control the surface heating. In this embodiment, a first PID controller interfaces with the tape heaters through a second PID controller. The first PID controller assigns the tape heater a temperature threshold and the second PID controller manages the power required for the tape heaters to reach the temperature threshold. The controller 420 may manually adjust the temperature thresholds in real-time as needed. The surface heater temperature thresholds may be independent of or may be based on T1, T2, T3, and T4. In one embodiment, the temperature thresholds are based on the conductivity of the sample trays, or based on the maximum temperature capacity of the sample trays (for instance, the maximum temperature at which the sample trays can be exposed before damage is done to the sample trays).

In another embodiment, in place of using sample trays, samples comprising reagents (e.g., PCR reagents) can be held in tubes made of glass or another material capable of efficiently conducting heat and compatible with any reagents to be heated and cooled by the solid state heat exchanger. In preferred embodiments, at least a portion of the surface of the sample holder will be made of a material that allows detection of the reaction products, either after the reaction is complete or in real-time, without removal of the sample. For example, real-time PCR relies on the use of fluorescent moieties whose emissions, which increase during the course of the reaction, can be detected by a suitable detector. Any methods for detecting the products of PCR reactions taking place in the sample holders, in real-time or otherwise, are known in the art and can be used with the fast thermal cycler of the present invention. Likewise, detection can take place in or out of the sample holders after the reaction is completed (e.g., after thermal cycling is completed).

Additional Considerations

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

In addition, the language used in the specification has been principally selected for readability and instructional purposes, and may not have been selected to delineate or circumscribe the inventive subject matter. Accordingly, the disclosure is intended to be illustrative, but not limiting, of the scope of the embodiments.

While particular embodiments and applications have been illustrated and described herein, it is to be understood that the embodiment is not limited to the precise construction and components disclosed herein and that various modifications, changes, and variations may be made in the arrangement, operation, and details of the methods and apparatuses without departing from the spirit and scope.

What is claimed is:

1. A method for thermally cycling a material, comprising:
   receiving a sample in each of a first set of wells and each of a second set of wells, each well in the first set of wells and the second set of wells coupled to a plurality of thermoelectric elements, wherein, for each well in the first set of wells, the well is coupled to a first subset of thermoelectric elements, and wherein each thermoelectric element in the first subset of thermoelectric elements is coupled to a different well in the second set of wells;
   retrieving electric current from a power module coupled to the thermoelectric elements;
   transferring thermal energy from the first set of wells to the second set of wells by flowing current through the thermoelectric elements in a first direction in a first operating mode; and
   transferring thermal energy from the second set of wells to the first set of wells by flowing current through the thermoelectric elements in a second direction in a second operating mode.

2. The method of claim 1, wherein the thermoelectric elements each comprise a first node and a second node, wherein the first node is configured to transfer thermal energy to and from a first well via heat conduction, and wherein the second node is configured to transfer thermal energy to and from a second well via heat conduction.

3. The method of claim 1, further comprising:
   determining the amount of thermal energy in a first well in the first set of wells using one or more sensors coupled to the first well.

4. The method of claim 3, further comprising:
   switching the direction of the current flowing through a thermoelectric element coupled to the first well from the first direction to the second direction responsive to the determined thermal energy in the first well falling below a first threshold.

5. The method of claim 3, further comprising:
   switching the direction of the current flowing through a thermoelectric element coupled to the first well from the second direction to the first direction responsive to the determined thermal energy in the first well exceeding a second threshold.

6. An apparatus for thermally cycling a material, comprising:
   a power module configured to provide electric current;
   a first set of wells;
   a second set of wells; and
   a plurality of thermoelectric elements, each thermoelectric element coupled to a first well in the first set of wells, a second well in the second set of wells and the power module, each thermoelectric element configured to:
      transfer thermal energy from the first well to the second well when current flows through the thermoelectric element in a first direction; and
      transfer thermal energy from the second well to the first well when current flows through the thermoelectric element in a second direction;
      wherein, for each well in the first set of wells, the well is coupled to a first subset of thermoelectric elements, and wherein each thermoelectric element in the first subset of thermoelectric elements is coupled to a different well in the second set of wells.

7. The apparatus of claim 6, wherein each thermoelectric element comprises a first node and a second node, wherein the first node is configured to transfer thermal energy to and from the first well via heat conduction, and wherein the second node is configured to transfer thermal energy to and from the second well via heat conduction.

8. The apparatus of claim 6, further comprising a controller coupled to each thermoelectric element and configured to switch the direction of the current flowing through each thermoelectric element.

9. The apparatus of claim 8, further comprising one or more sensors coupled to the first set of wells, the one or more sensors configured to:
   determine the amount of thermal energy in a first well of the first set of wells; and
   communicate the determined amount of thermal energy to the controller.

10. The apparatus of claim 9, wherein the controller is further configured to:
    switch the direction of the current flowing through the thermoelectric elements from the first direction to the second direction responsive to the determined thermal energy in the first well falling below a first threshold.

11. The apparatus of claim 9, wherein the controller is further configured to:
    switch the direction of the current flowing through the thermoelectric elements from the second direction to the first direction responsive to the determined thermal energy in the first well exceeding a second threshold.

12. The apparatus of claim 6, wherein for each well in the second set of wells, the well is coupled to a second subset of thermoelectric elements, and wherein each thermoelectric element in the second subset of thermoelectric elements is coupled to a different well in the first set of wells.

13. The apparatus of claim 6, wherein the first set of wells and the second set of wells are configured to receive a sample tray, the sample tray comprising one or more wells, and wherein the sample tray wells are inserted into the first set of wells and the second set of wells when the sample tray is placed upon the first set of wells and the second set of wells.

\* \* \* \* \*